United States Patent [19]
Kintner

[11] Patent Number: 4,516,969
[45] Date of Patent: May 14, 1985

[54] CONTROL SYRINGE

[75] Inventor: Michael H. Kintner, Manville, N.J.

[73] Assignee: Medtech Plastics, Inc., South Plainfield, N.J.

[21] Appl. No.: 484,863

[22] Filed: Apr. 14, 1983

[51] Int. Cl.³ .............................................. A61M 5/00
[52] U.S. Cl. ..................................... 604/187; 604/227
[58] Field of Search ............... 604/227, 187, 407, 218; 141/27

[56] References Cited

U.S. PATENT DOCUMENTS

| | | | |
|---|---|---|---|
| 1,155,012 | 9/1915 | Slee | 604/227 |
| 3,380,489 | 4/1968 | Harautuneian | 141/27 |
| 3,934,584 | 1/1976 | Corio | 604/218 |
| 4,253,501 | 3/1981 | Ogle | 604/407 |

Primary Examiner—John D. Yasko
Attorney, Agent, or Firm—Lawrence E. Sklar

[57] ABSTRACT

A barrel for a control syringe, including a substantially cylindrical body, a pair of horizontal flanges extending from the top of the cylindrical body, each of the horizontal flanges having an aperture therein adjacent the cylindrical body, and a pair of substantially horizontal flanges extending from the cylindrical body and located below the apertures in the horizontal flanges. The sides of the apertures are substantially the same shape as the sides of the substantially horizontal flanges.

A single mold cavity and an integral core pin for forming the control syringe barrel are also disclosed.

5 Claims, 10 Drawing Figures

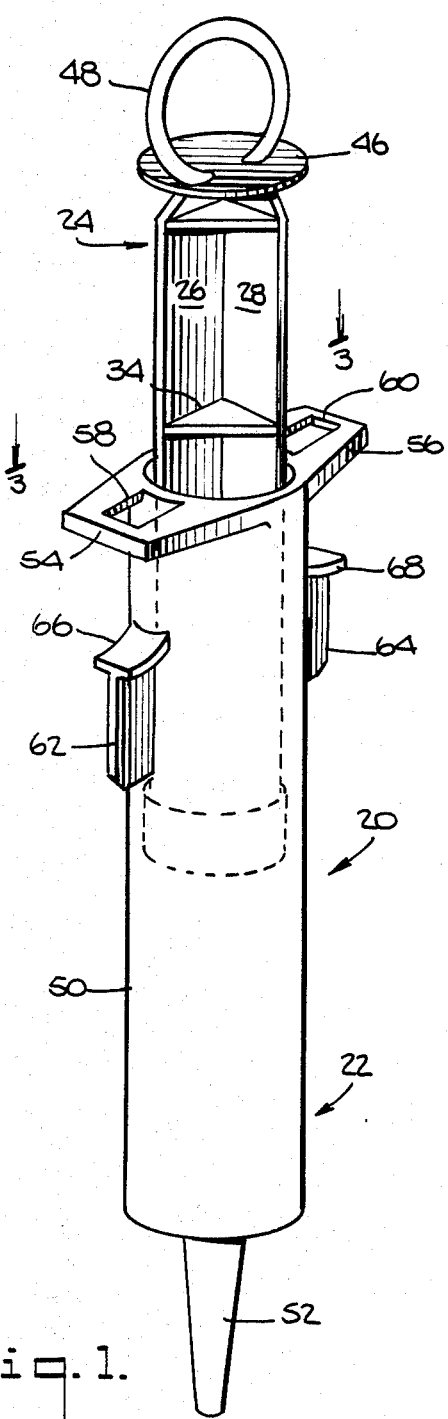
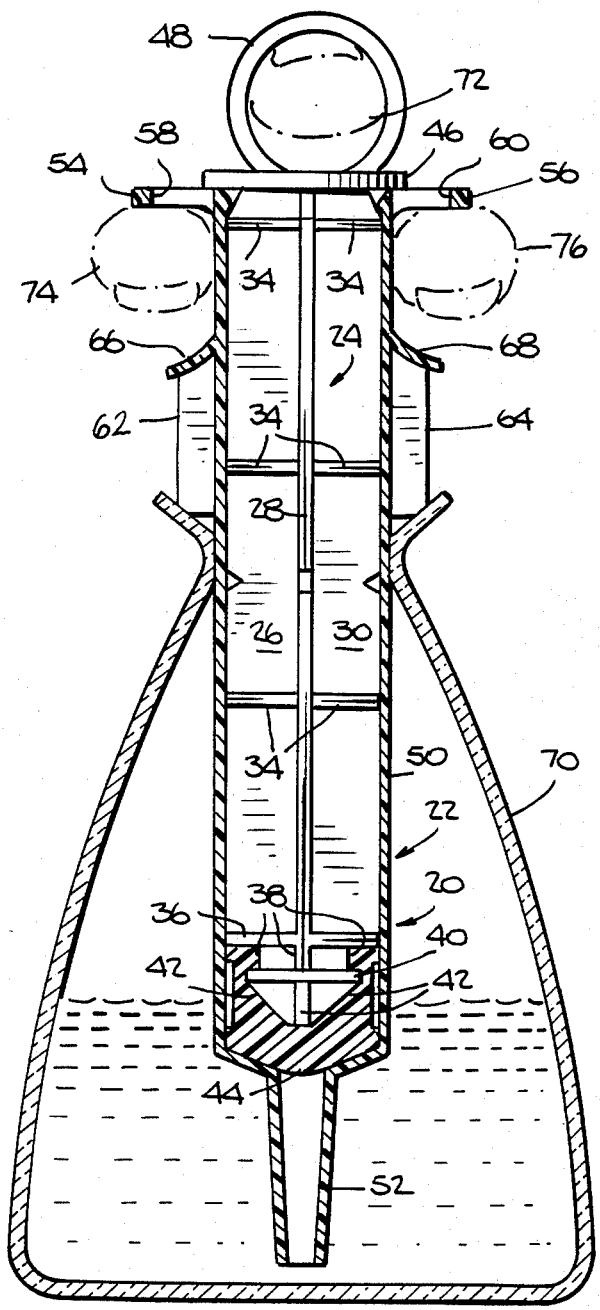
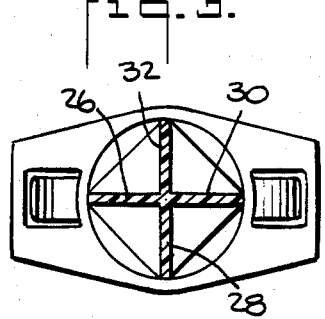

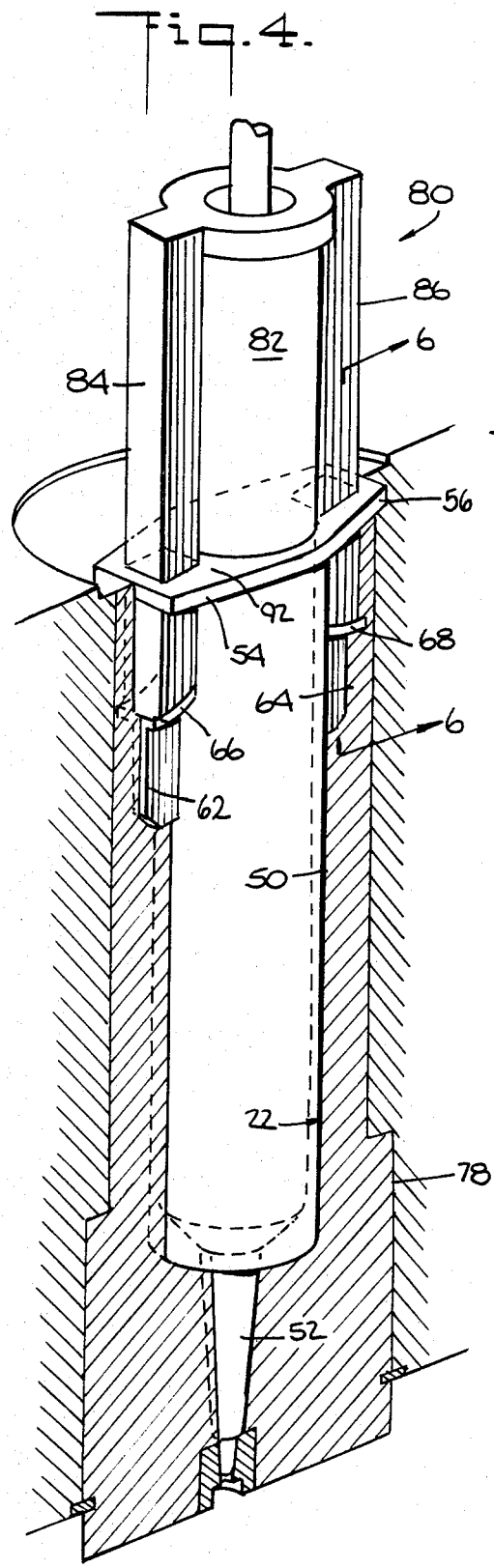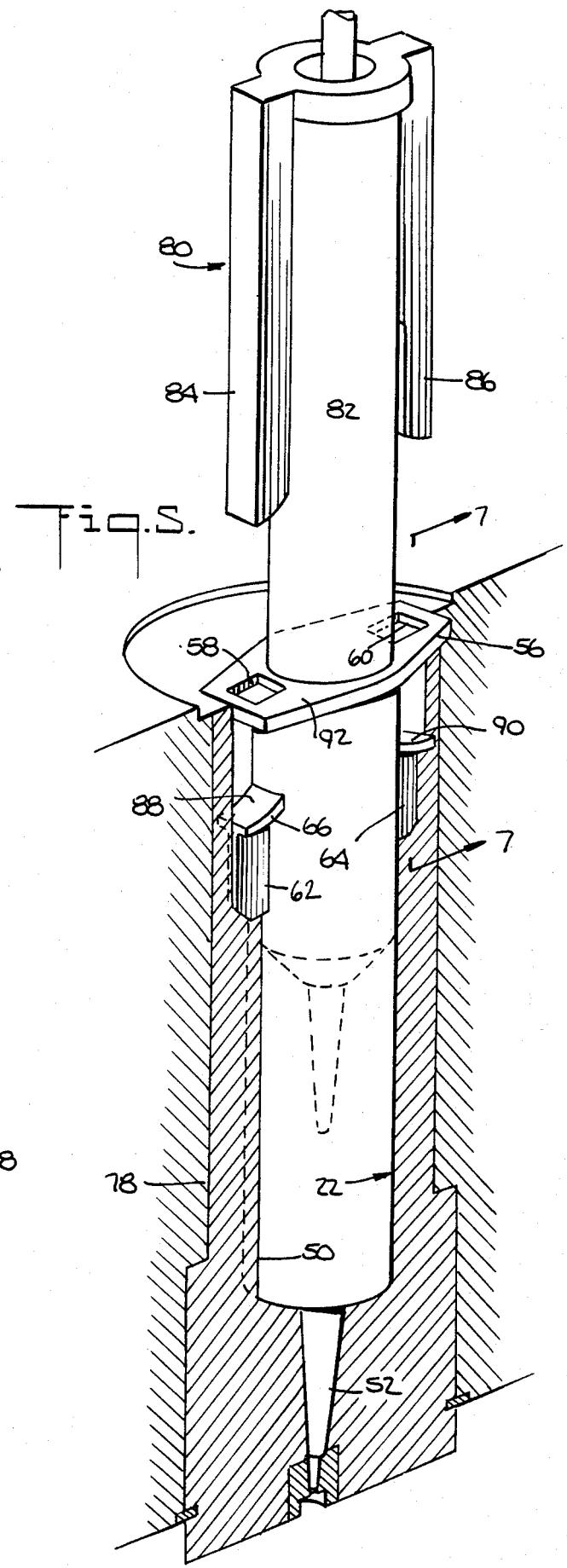

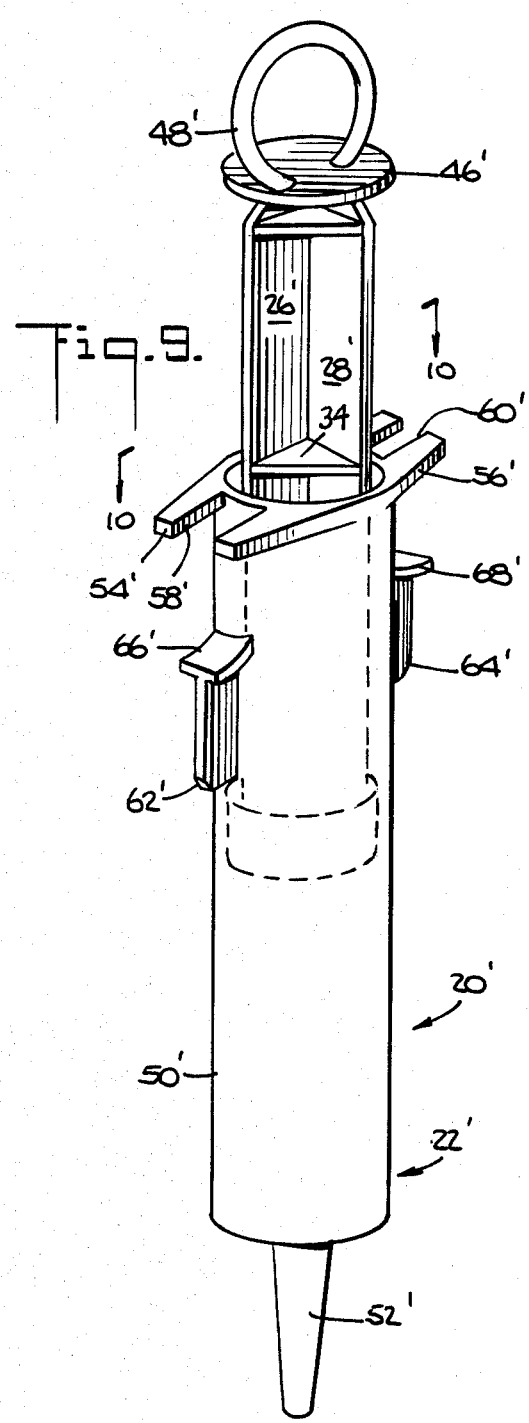
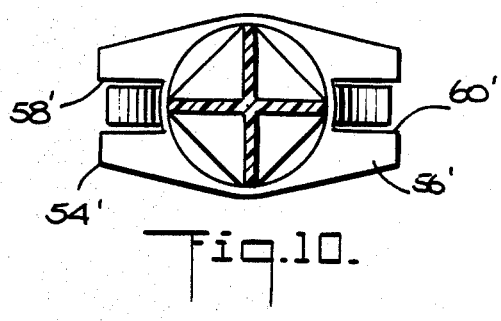
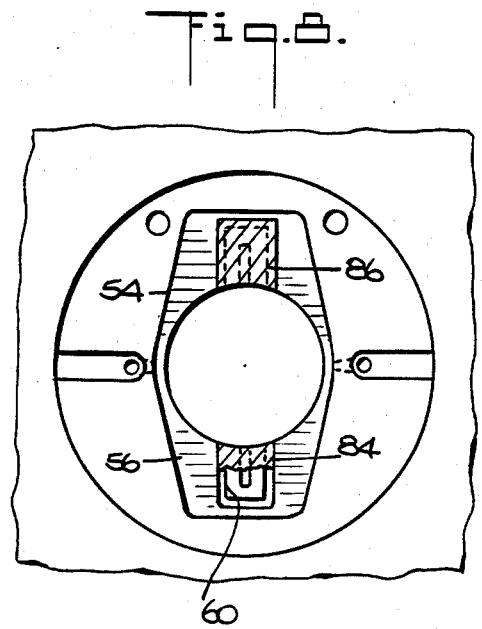
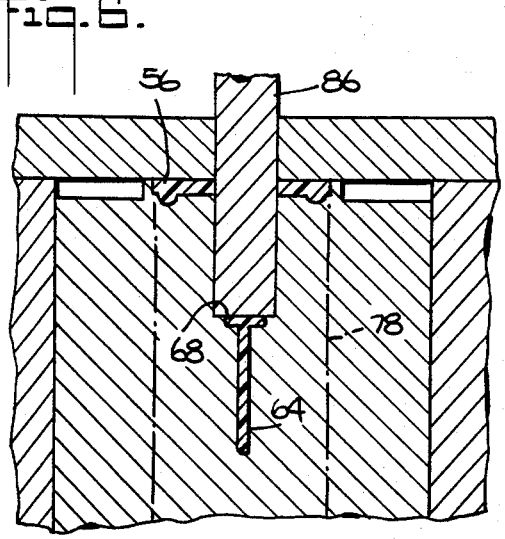
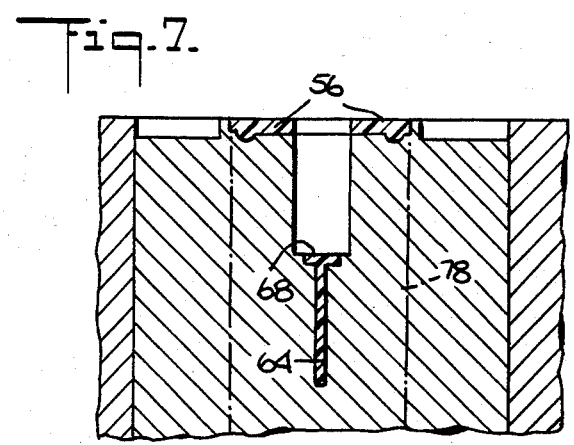

CONTROL SYRINGE

BACKGROUND OF THE INVENTION

The instant invention relates to hypodermic control syringes, i.e. syringes for irrigation, injection and suction, and more particularly to such a syringe that can be used with one hand.

Normal syringes are used only to inject fluids whereas control syringes are used both for injection (irrigation) and removal (suction) of fluids in tissue. Often a physician or nurse has only one hand free with which to operate a control syringe, which means that only one hand is available to push the plunger down into the barrel for irrigation and for pulling the plunger up the barrel for suction.

Heretofore control syringes designed for one-hand operation have employed a thumb ring attached to the end of the plunger and two finger rings attached to the syringe barrel. In operation, the index and middle fingers were positioned within these two finger rings and the thumb in the thumb ring. These three-ringed syringes, however, have not proven satisfactory. One problem has been the difficulty in threading the index finger, the middle finger and the thumb through the three separate rings. Another problem has been a feeling of instability once the syringe is on the hand, because the rings are relatively thin and in most cases are much larger than the diameter of the fingers and thumb. Furthermore, because of the larger finger rings projecting from opposite sides of the barrel, the syringe must be nearly twice as wide as the package for a conventional syringe. The three-ringed syringe presents a manufacturing problem in that complicated molds are required to accommodate the unwieldy syringe structure.

Accordingly, the instant invention overcomes all of the foregoing problems by providing a control syringe which can be conveniently operated by one hand and a syringe barrel which can be manufactured using a single mold cavity and core pin, i.e. a two part mold, and apparatus for manufacturing such a syringe barrel.

SUMMARY OF THE INVENTION

In accordance with the instant invention, there is provided a control syringe barrel which includes a substantially cylindrical body, a pair of horizontal flanges extending from the top of the cylindrical body, each of the horizontal flanges having an aperture therein adjacent the cylindrical body, and a pair of substantially horizontal flanges extending from the cylindrical body and located below the apertures in the horizontal flanges, and wherein the sides of the apertures are substantially the same shape as the sides of the substantially horizontal flanges.

In accordance with the instant invention, there is also provided apparatus for forming a control syringe barrel having a pair of upper and lower flanges. The apparatus includes a mold cavity for forming most of the outer surface of the syringe barrel, and an integral core pin having a cylindrical core section for forming the inner surface of the syringe barrel and a pair of vertically extending ribs spaced from said cylindrical core section for forming the top surface of the lower flanges and the outer surface of the syringe barrel directly above the lower flanges. The vertically extending ribs also form an aperture in each of the upper flanges.

BRIEF DESCRIPTION OF THE DRAWINGS

FIG. 1 is a perspective view of a control syringe in accordance with the instant invention;

FIG. 2 is a vertical sectional view of the syringe seen in FIG. 1 sitting in an irrigation bottle and showing the user's fingers;

FIG. 3 is a sectional view taken on the plane indicated by the line 3—3 in FIG. 1;

FIG. 4 is a perspective view of the mold and core pin for molding the syringe barrel, the front half of the mold being cut away, showing the core pin fully inserted within the mold and the cavity between the core pin and the mold filled with plastic;

FIG. 5 is similar to FIG. 4 except it shows the core pin withdrawn from the mold after the control syringe has been formed in the mold;

FIG. 6 is a sectional view taken on the plane indicated by the line 6—6 in FIG. 4;

FIG. 7 is a sectional view taken on the plane indicated by the line 7—7 in FIG. 5;

FIG. 8 is a plan view of FIG. 6;

FIG. 9 is a perspective view of an alternative embodiment of a control syringe in accordance with the instant invention; and FIG. 10 is a sectional view taken on the plane indicated by the line 10—10 in FIG. 9.

DETAILED DESCRIPTION

In describing the preferred embodiment of the instant invention, reference is made to the drawings, wherein there is seen in FIGS. 1 and 2 a control syringe generally designated 20 consisting of a barrel 22 and a plunger 24. The design of the plunger 24 is conventional and includes four vertical ribs 26, 28, 30 and 32 (see FIG. 3) having horizontal, triangular reinforcements 34. The bottom of the plunger 24 concludes with a circular section 36 (see FIG. 2), four vertical, rectangular sections 38, a smaller, horizontal circular section 40, and four vertical, triangular sections 42. An integral bottom member 44 fits over the lower portion of the plunger 24. The top of the plunger 24 consists of a circular section 46 and a ring 48 for receiving the thumb 72 of the user.

The barrel 22 of the syringe 20 consists of a cylindrical section 60 having a truncated, conical nose portion 52 at one end for receiving a hypodermic needle (not shown) when it is desired to use a needle and a pair of horizontal flanges 54 and 56 at the other end. It should be noted that the syringe 20 may be used without a needle. Each of the flanges 54 and 56 includes an aperture 58 and 60 respectively. Located on the side of the cylindrical section 50 below the horizontal flanges 54 and 56 are a pair of vertical substantially straight flanges 62 and 64 respectively. Each of the vertical flanges 62 and 64 includes a substantially horizontally extending flange 66 and 68 respectively contiguous therewith. It should be understood that the vertical flanges 62 and 64 are not necessary for the formation of the flanges 66 and 68, and that the flanges 66 and 68 can assume virtually any shape or size within the constraints imposed by the size and shape of the flanges 54 and 56, as discussed further hereinbelow.

Use of the control syringe 20 is probably best understood by referring to FIG. 2, wherein the syringe 20 is seen standing in an irrigation bottle 70. It can be seen that the bottoms of the flanges 62 and 64 are so designed as to support the syringe 20 in an upright position when it is inserted in the irrigation bottle 70. When it is desired to use the syringe 20, the thumb 72 is inserted in the thumb ring 48, the index finger 74 is placed between the horizontal flanges 54 and 66 and the middle finger 76 is placed between the horizontal flanges 56 and 68. When it is desired to pull the plunger 24 upward, the flanges 66 and 68 prevent the index finger 74 and the middle finger 76 from sliding down the side of the barrel 22. When it is desired to push the plunger 24 downward, the flanges 54 and 56 rest on the fingers 74 and 76 respectively in conventional manner.

As explained hereinabove, the syringe barrel 22 is so designed that it can be molded from a single, integral mold cavity and a single, integral core pin. Referring now to FIGS. 4 and 5, there is seen an integral mold 78 which is essentially conventional in design and which forms most of the outer surface of the barrel 22. An integral core pin 80 comprising a cylindrical core section 82 and a pair of vertically extending ribs 84 and 86 spaced from the cylindrical core section 82 is used to form the inner surface of the barrel 22 in conventional manner. The top surfaces 88 and 90 of the flanges 66 and 68 (see FIG. 5) respectively and the outer surface of the barrel 22 directly above the flanges 66 and 68 are formed by the ribs 84 and 86 respectively. A stripping plate (not shown) may be used to form the top surface 92 of the flanges 54 and 56. The result of using the ribs 84 and 86 are the apertures 58 and 60 in the flanges 54 and 56 respectively. Since the apertures 56 and 58 as well as the top surfaces 88 and 90 of the flanges 66 and 68 respectively are formed by the ribs 84 and 86, the sides of the aperture 56 and the sides of the flange 90 are parallel and have the same shape, and the sides of the aperture 58 and the sides of the flange 88 are parallel and have the same shape.

In FIG. 9 an alternative embodiment is seen which is identical to the embodiment shown in FIG. 1 except that the apertures 58' and 60' are open at their extremities.

Various modifications and changes are contemplated and may obviously be resorted to, without departing from the spirit or scope of the invention as hereinafter defined by the appended claims.

What is claimed is:

1. A control syringe barrel, comprising:
    a substantially cylindrical body;
    a pair of opposing, horizontal flanges extending from the top of the cylindrical body;
    a pair of opposing, substantially horizontal flanges extending from the cylindrical body and located below the horizontal flanges; and
    a substantially straight vertical flange located beneath each of the substantially horizontal flanges and contiguous therewith and with said cylindrical body said substantially straight vertical flange having a surface radially remote from and parallel to the axis of said cylindrical body, said surface extending substantially the entire length of said vertical flange.

2. The control syringe barrel of claim 1, wherein each of said horizontal flanges includes an aperture therein adjacent said cylindrical body.

3. The control syringe barrel of claim 1, wherein the apertures are open at their extremities remote from the cylindrical body.

4. The control syringe barrel of claim 1, wherein the apertures are substantially rectangular.

5. The control syringe barrel of claim 1, wherein the bottom edges of said vertical flanges are substantially horizontal.

* * * * *